(12) United States Patent
Müller et al.

(10) Patent No.: US 6,623,963 B1
(45) Date of Patent: Sep. 23, 2003

(54) CELLULAR MATRIX

(75) Inventors: Peter Karl Müller, Auf dem Vorbeck 25, 29562 Lübeck (DE); Peter Behrens, Aegidiensir 51, 23552 Lübeck (DE); Bruno Giannetti, Bonn (DE); Jürgen Rohwedel, Huexatr 112-116, 23552 Lübeck (DE); Martin Russlies, Gustav-Falke-Sir 16B, 23562 Lübeck (DE)

(73) Assignees: Verigen AG (DE); Peter Karl Muller (DE); Peter Behrens (DE); Jurgen Rohwedel (DE); Martin Russlies (DE)

( * ) Notice: Subject to any disclaimer, the term of this patent is extended or adjusted under 35 U.S.C. 154(b) by 0 days.

(21) Appl. No.: 09/467,584

(22) Filed: Dec. 20, 1999

(51) Int. Cl.$^7$ .................................................. C12N 5/00
(52) U.S. Cl. .................. 435/395; 435/401; 424/426; 530/326; 623/23.72
(58) Field of Search ................................ 435/395, 401; 530/326; 424/426; 623/23.72

(56) References Cited

U.S. PATENT DOCUMENTS

| | | |
|---|---|---|
| 3,949,073 A | 4/1976 | Daniels et al. |
| 4,066,083 A | 1/1978 | Ries |
| 4,394,370 A | 7/1983 | Jefferies |
| 4,424,208 A | 1/1984 | Wallace et al. |
| 4,472,840 A | 9/1984 | Jefferies |
| 4,488,911 A | 12/1984 | Luck et al. |
| 4,582,640 A | 4/1986 | Smestad et al. |
| 4,642,117 A | 2/1987 | Nguyen et al. |
| 4,882,149 A | 11/1989 | Spector |
| 4,931,546 A | 6/1990 | Tardy et al. |
| 5,076,265 A | 12/1991 | Wokalek |
| 5,116,374 A | 5/1992 | Stone |
| 5,158,574 A | 10/1992 | Stone |
| 5,201,745 A | 4/1993 | Tayot et al. |
| 5,206,028 A | 4/1993 | Li |
| 5,258,043 A | 11/1993 | Stone |
| 5,618,551 A | 4/1997 | Tardy et al. |
| 5,677,284 A | 10/1997 | Li |
| 5,735,902 A | 4/1998 | Li et al. |
| 5,837,278 A | 11/1998 | Geistlich et al. |
| 5,842,477 A | 12/1998 | Naughton et al. |
| 5,902,741 A | 5/1999 | Purchio et al. |

FOREIGN PATENT DOCUMENTS

| | | |
|---|---|---|
| EP | 0 674 908 A1 | 10/1995 |
| WO | WO 90/05755 | 5/1990 |
| WO | WO 90/13302 | 11/1990 |
| WO | WO 92/13565 | 8/1992 |
| WO | WO 93/19168 | 9/1993 |
| WO | WO 96/24310 | 8/1996 |
| WO | WO 96/25961 | 8/1996 |
| WO | WO 97/32616 | 9/1997 |
| WO | WO 98/15299 | 4/1998 |
| WO | WO 98/34656 | 8/1998 |
| WO | WO 99/06080 | 2/1999 |
| WO | WO 99/19005 | 4/1999 |

OTHER PUBLICATIONS

The Merck Index, Encyclopedia of Chemicals, Drugs, and Biologicals, Index No. 2476 Collagen, Published by Merck & Co., Inc., pp. 387–388, 1989.

M. D. Miller, "Treatment of chondral injuries", Operative Techniques in Orthopaedics, vol. 7, No. 4, Oct. 1997, pp. 261–262.

J. A. Buckwalter, "Chondral and osteochondral injuries: mechanisms of injury and repair responses", Operative Techniques in Orthopaedics, vol. 7, No. 4, Oct. 1997, pp. 263–269.

Suh et al., "Injury and repair or articular cartilage: related scientific issues", Operative Techniques in Orthopaedics, vol. 7, No. 4, Oct. 1997, pp 270–278.

J. M. Linklater et al., "Imaging of chondral defects", Operative Techniques in Orthopaedics, vol. 7, No. 4, Oct. 1997, pp 279–288.

M. D. Miller, "Atlas of chondral injury treatment", Operative Techniques in Orthopaedics, vol. 7, No. 4, Oct. 1997, pp 289–293.

J.M. Bert, "Abrasion arthroplasty", Operative Techniques in Orthopaedics, vol. 7, No. 4, Oct. 1997, pp 294–299.

J.R. Steadman et al., "Microfracture technique for full–thickness chondral defects: technique an dclinical results", Operative Techniques in Orthopaedics, vol. 7, No. 4, Oct. 1997, pp 300–304.

K. R. Stone et al., "Surgical technique for articular cartilage transplantation to full–thickness cartilage defects in the knee joint", Articular Cartilage Transplantation, 1997, pp 305–311.

L. Hangody et al., "Osteochondral plugs: autogenous osteochondral mosaicplasty for the treatment of focal chondral and osteochondral articular defects", Operative Techniques in Orthopaedics, vol. 7, No. 4, Oct. 1997, pp 312–322.

T. Minas et al., "Chondrocyte transplantation", Operative Techniques in Orthopaedics, vol. 7, No. 4, Oct. 1997, pp 323–333.

A. E. Gross, "Fresh osteochondral allografts for post–traumatic knee defects: surgical technique", Operative Techniques in Orthopaedics, vol. 7, No. 4, Oct. 1997, pp 334–339.

(List continued on next page.)

*Primary Examiner*—Leon B. Lankford, Jr.
(74) *Attorney, Agent, or Firm*—Morgan, Lewis & Bockius, LLP (57) ABSTRACT

A biocompatible, resorbable Type II collagen-based matrix is reconstituted from solubilized animal cartilage tissue and used in the culture and growth of cells, such as chondrocyte cells. The matrix is produced by isolating cartilage tissue, solubilizing and reconstituting the cartilage to form a fleece-like material, pressing the fleece-like material to form a sheet-like article, and sterilizing the article. An implantable article for cartilage repair includes chondrocyte cells retained on the matrix.

8 Claims, 6 Drawing Sheets

OTHER PUBLICATIONS

F. R. Convery et al., "The operative technique of fresh osteochondral allografting of the knee", Operative Techniques in Orthopaedics, vol. 7, No. 4, Oct. 1997, pp. 340–344.

B. Zarins et al., "Chondral injuries: clinical overview", Operative Techniques in Orthopaedics, vol. 7, No. 4, Oct. 1997, pp 345–346.

$2^{nd}$ Symposium International Cartilage Repair Society, Boston Marrriott Long Wharf, Nov. 16–18, 1998.

Stone et al., "Regeneration of Meniscal Cartilage with Use of a Collagen Scaffold", Journal of Bone and Joint Surgery, vol. 79–A, No. 12, Dec. 1997, pp. 1770–1777.

Nehrer et al., "Canine Chondrocytes Seeded in Type I and Type II Collagen Implants Investigated in Vitro", Journal of Biomedical Materials Research, vol. 38, 1997, pp. 95–104.

Toolan et al., "Effects of growth–factor–enhanced culture on a chondrocyte–collagen implant for cartilage repair" Journal of Biomedical Materials Research, vol. 31, 1996, pp. 273–280.

Fujisato et al., "Effect of basic fibroblast growth factor on cartilage regeneration in chondrocyte–seeded collagen sponge scaffold", Biomaterials, vol. 17, No. 2, 1996, pp. 155–162.

van Susante et al., "Culture of chondrocytes in alginate and collagen carrier gels", Acta Orthop Scand, vol. 66, No. 6, 1995, pp. 549–556.

Wakitani et al., "Repair of Rabbit Articular Surfaces with Allograft Chondrocytes Embedded in Collagen Gel", The Journal of Bone and Joint Surgery, vol. 71–B, No. 1, 1989, pp. 74–80.

Nehrer et al., "Chondrocyte–seeded collagen matrices implanted in a chondral defect in a canine model", Biomaterials, vol. 19, 1998, pp. 2313–2328.

COOMASSIE STAINING    IMMUNOBLOT (COLLAGEN II)

CELLULAR MATRIX

FIELD OF THE INVENTION

The present invention relates to a matrix suitable, inter alia, for the support, retention, and/or growth of living cells in a form suitable, for example, for cell transplantation. More particularly, it pertains to a reconstituted collagen matrix suitable for cell growth, such as chondrocyte cell growth for use in chondrocyte cell transplantation.

BACKGROUND OF THE INVENTION

Injuries to the cartilage of the knee or other joints often result from abnormal mechanical loads which deform the tissue matrix. The loads applied to the joint can rupture the collagen network in the matrix and decrease the stiffness of the tissue.

Cartilage injuries are difficult to treat because articular cartilage has a limited capacity for regeneration once it has been damaged. Type II collagen is the main structural protein of the extracellular matrix in articular cartilage. Type II collagen, similar to other types of collagen, is comprised of three collagen polypeptides which form a triple helix configuration. The polypeptides are intertwined with each other and possess at each end telopeptide regions which provide the crosslinking between the collagen polypeptides. Collagen matrices in their natural state contain numerous crosslinked triple helices and the individual molecules have a molecular weight of about 300,000 daltons. Type II collagen is found almost exclusively in animal cartilage, while other types of collagen are found in animal hides, membranes, and bones.

Excessive degradation of Type II collagen in the outer layers of articular surfaces of joints is also caused by osteoarthritis. The collagen network is accordingly weakened and subsequently develops fibrillation whereby matrix substances, such as proteoglycans, are lost and eventually displaced entirely. Such fibrillation of weakened osteoarthritic cartilage can reach down to the calcified cartilage and into the subchondral bone (Kempson, G. E. et al., Biochim. Biophys. Acta 1976, 428, 741; Roth, V. and Mow, V. C., J. Bone Joint Surgery, 1980, 62A, 1102; Woo, S. L. -Y. et al., in *Handbook of Bioengineering* (R. Skalak and S. Chien Eds), McGraw-Hill, New York, 1987, pp. 4.1–4.44).

A method for regeneration-treatment of cartilage would be useful for treating arthritis and other joint conditions and could be performed at an earlier stage of joint damage, thus reducing the number of patients needing more extensive procedures, such as artificial joint replacement surgery. With such preventive methods of treatment, the number of patients developing osteoarthritis would also decrease.

Methods for growing and using chondrocyte cells are described by Brittberg, M. et al. (New Engl. J. Med. 1994, 331, 889). Autologous transplants using cells grown with these methods are also disclosed. Additionally, Kolettas et al. examined the expression of cartilage-specific molecules, such as collagens and proteoglycans, under prolonged cell culturing (J. Cell Science 1995, 108, 1991). They found that, despite morphological changes during culturing in monolayer cultures (Aulthouse, A. et al., In Vitro Cell Dev. Biol., 1989, 25, 659; Archer, C. et al., J. Cell Sci. 1990, 97, 361; Hänselmann, H. et al., J. Cell Sci. 1994, 107, 17; Bonaventure, J. et al., Exp. Cell Res. 1994, 212, 97), when compared to suspension cultures grown over agarose gels, alginate beads or as spinner cultures (retaining a round cell morphology) tested by various scientists, such morphologies did not change the chondrocyte—expressed markers such as types II and IX collagens and the large aggregating proteoglycans, aggrecan, versican and link protein did not change (Kolettas, E. et al., J. Cell Science 1995, 108, 1991).

In addition, chondrocyte cells from donors have been grown in vitro to form neocartilage which has been implanted into animals (Adkisson et al., "A Novel Scaffold-Independent Neocartilage Graft for Articular Cartilage Repair," ICRS $2^{nd}$ Symposium International Cartilage Repair Society, Nov. 16–18, 1998). Further, chondrocyte cells have been seeded onto the cartilage surface of osteochondral cores to attempt cartilage regeneration (Albrecht et al., "Circumferential Seeding of Chondrocytes: Towards Enhancement of Integrative Cartilage Repair," ICRS $2^{nd}$ Symposium International Cartilage Repair Society, Nov. 16–18, 1998). Articular surface defects in knee joints have been treated with various cultured chondrocytes (Stone et al., Operative Techniques in Orthopaedics 7(4), pp. 305–311, October 1997 and Minas et al., Operative Techniques in Orthopaedics 7(4), pp. 323–333, October 1997).

Membranes and certain of their general properties are described in the following references:

U.S. Pat. No. 5,837,278—Geistlich et al. describe a collagen-containing membrane which is resorbable and is used in guided tissue regeneration. The membrane has a fibrous face which allows cell growth thereon and a smooth face opposite the fibrous face which inhibits cell adhesion thereon. The membrane product is derived from a natural collagen membrane (from the hide or tendons of calves or piglets) and, although treated, it is described as maintaining its natural structural features. The collagen is purified with alkaline agents to defat the collagen and degrade substances, and then the purified collagen is acidified, washed, dried, degreased, and optionally crosslinked. The fats are saponified. The membrane is described as containing about 95% by weight native collagen.

PCT WO 96/25961—Geistlich et al. describe a matrix for reconstructing cartilage tissue which consists of Type II collagen, optionally including crosslinking. In producing the matrix, cartilage is taken from an animal and frozen, subjected to size reduction, dewatered, defatted, washed, and treated with alkaline materials. Non-collagen alkaline soluble proteins are denatured, destroyed, dissolved, and eliminated. Dialysis and freeze drying are mentioned as possible treatment steps. The matrix material is stamped to form a required shape and then it is sterilized.

U.S. Pat. No. 4,424,208—Wallace et al. describe an injectable collagen implant material comprising particulate crosslinked atelopeptide collagen and reconstituted atelopeptide collagen fibers dispersed in an aqueous carrier. The atelopeptide form of collagen lacks the native telopeptide crosslinking. In the method described in the '208 patent, collagen obtained from bovine or porcine corium (subepithelial skin layer) is softened by soaking in a mild acid; depiliated; comminuted by physical treatment, such as grinding; solubilized by treatment with acid and a proteolytic enzyme; treated with an alkaline solution; and freed of enzyme. The crosslinked gel form of collagen is formed by radiation-induced or chemical-induced crosslinking, such as by addition of glutaraldehyde. Meanwhile, the fibrous form of collagen is produced by neutralizing the solution with a buffer, such as $Na_2HPO_4$. The collagen content of the injectable implant comprises 5–30% fibrous collagen and 70–98% of the crosslinked gel form of collagen.

U.S. Pat. No. 4,488,911—Luck et al. describe the formation of collagen fibers free of the immunogenic, telopeptide portion of native collagen. The telopeptide region provides points of crosslinking in native collagen. The fibers, which may be crosslinked, are described for use as sponges, prosthetic devices, films, membranes, and sutures. In the method described in the '911 patent, (non-Type II; Type I and others) collagen obtained from tendons, skin, and connective tissue of animals, such as a cow, is dispersed in an acetic acid solution, passed through a meat chopper, treated with pepsin to cleave the telopeptides and solubilize the collagen, precipitated, dialyzed, crosslinked by addition of formaldehyde, sterilized, and lyophilized. The '911 patent indicates that its disclosed method obtains the atelocollagen form of collagen, free from noncollagen proteins, such as glycosaminoglycans and lipids. Further, it describes that the collagen may be used as a gel to make, for example, a membrane, film, or sponge and that the degree of crosslinking of the collagen can be controlled to alter its structural properties.

Notwithstanding the foregoing disclosures, applicants believe that there remains a need for a satisfactory and effective scaffold for cell growth, particularly chondrocyte cell growth.

BRIEF SUMMARY OF THE INVENTION

The present invention provides a reconstituted biocompatible, resorbable Type II collagen-based matrix for use, for example, as a scaffold on which cells, such as chondrocyte cells, can be cultured, and a method for producing the matrix. Furthermore, the matrix can be used as a sheet to cover small cartilage lesions or can be used in combination with cells other than chondrocytes (i.e., with mesenchymal stem cells). The Type II collagen of the matrix of the present invention is solubilized by breaking the crosslinking of the collagen through its telopeptide region into its non-crosslinked atelocollagen form. The matrix may be a support matrix which provides a scaffold on which cells can be grown and retained.

In one embodiment of the present invention, the matrix is produced by the reconstitution of animal cartilage tissue (horse, pig, cow (or calf), goat, chicken, or kangaroo) from the solubilization of the Type II collagen and removal of associated proteins and molecules from the tissue and the subsequent isolation, crosslinking, and lyophilization to form a fleece-like matrix.

In another embodiment, the matrix composition is formed from recombinantly produced Type II collagen which is solubilized and crosslinked to form a fleece-like matrix.

In still another embodiment, the matrix composition is used as a base for growing and attaching living cells, particularly chondrocyte cells, thereon. In this embodiment, chondrocytes cells adhere to the matrix and grow, substantially as they do in vivo.

In a further embodiment, the present invention provides an implantable article including chondrocyte cells retained on the support matrix and a method of making the same. In another embodiment, the present invention provides a method for tissue repair, particularly the effective treatment of articulating joint surface cartilage in an animal by the transplantation of an implantable article including chondrocyte cells, either autologous or homologous, retained on or combined with the support matrix.

BRIEF DESCRIPTION OF THE DRAWING

The present invention may be better understood by reference to the description which follows taken together with the accompanying figures which illustrate the present invention wherein.

DETAILED DESCRIPTION OF THE INVENTION

The present invention comprises a reconstituted Type II collagen matrix (hereinafter "scaffold" or "carrier matrix") which may be used, for example, as a support matrix for supporting the growth of cells, such as chondrocyte cells, and a process of producing the matrix. When crosslinked, the matrix has a fleece-like consistency which, when it is loaded with cells, can be implanted into a site in the body in need of repair (e.g., damaged tissue) and molded into the proper form for deposit at the site. In its non-crosslinked form, the matrix has a liquid or gel-like consistency. In fleece-like form, the matrix is reversibly deformable as it is handled by the user so that an implantable fabric comprising the matrix can be manipulated to facilitate implantation; it then remains at the site of implantation.

The Type II collagen matrix is obtained by reconstituting previously solubilized animal cartilage tissue, from an animal, such as a horse, pig, cow (or calf), goat, chicken, or kangaroo. The cartilage tissue obtained from the animal is solubilized by physical and/or chemical treatment. The solubilization process includes treatment with various buffers to remove impurities and to separate the solid and liquid phases; physical treatment to separate solid and liquid phases, such as by centrifugation; and treatment with a proteolytic enzyme that breaks the crosslinking of the collagen in its telopeptide region into its virtually non-crosslinked, atelocollagen, triple helix form.

By reconstituting, it is meant that the non-crosslinked, atelocollagen form of collagen reestablishes its crosslinking between the variable regions along the collagen molecule, including some remaining residues in the telopeptide region. As a result, the collagen loses its liquid or gel-like consistency and becomes more rigid with a higher degree of structural integrity such that it may be a scaffold for the growth of cells thereon.

Figure 3:
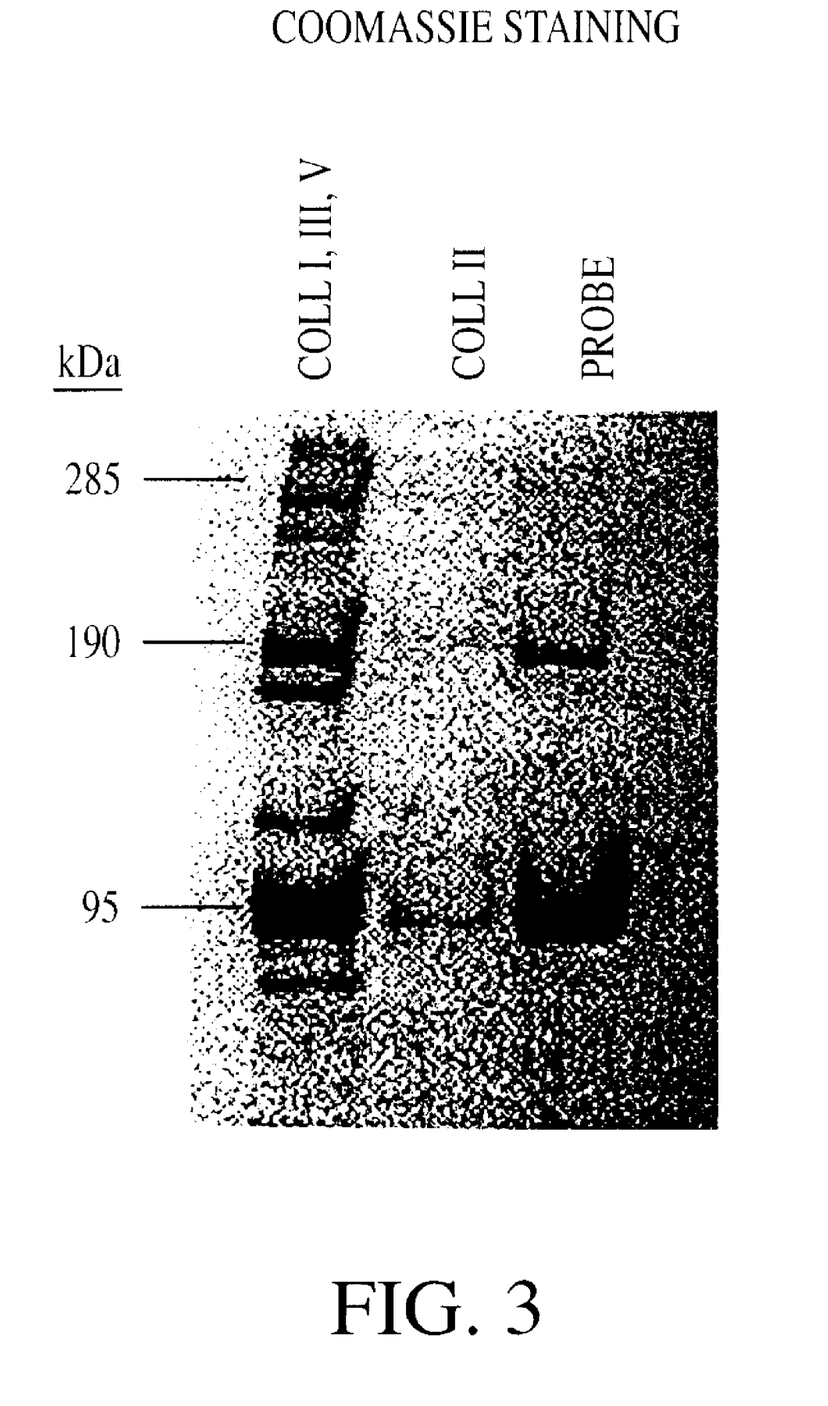
FIG. 3 displays the results of an electrophoretic gel showing the different sizes of Type II collagen chains used in the matrix of the present invention.
Figure 4:
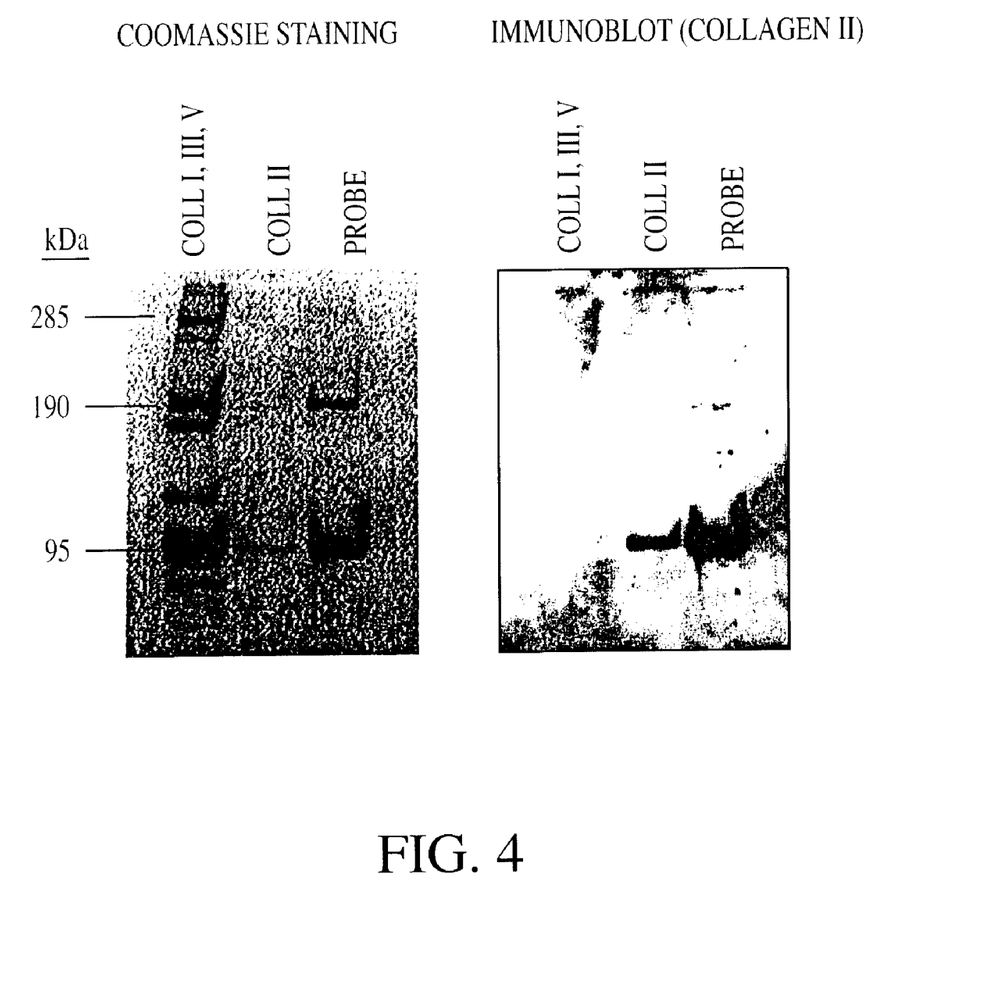
FIG. 4 displays the results of two electrophoretic gels showing the different sizes of bands for the Type II collagen used in the matrix of the present invention.

FIGS. 3 and 4 display the results of a gel electrophoresis study of the cartilage in different forms, showing crosslinked and non-crosslinked, atelocollagen chains. The 95 kDA band represents the non-crosslinked atelocollagen and the 190 kDA and 285 kDA bands represent various degrees of crosslinking of the collagen. FIGS. 3 and 4 confirm that, in the method of producing the matrix of the present invention, collagen is broken into its constituent, non-crosslinked, Type II collagen chains. The bands shown in FIG. 3 represent alpha (monomers) (95 kDa), beta (dimers) (190 kDa), and gamma (trimers) (285 kDa) of Type II collagen α1(II)-chains. The immunoblot of FIG. 4 underlines and proves that the nature of the bands shown in FIG. 3 are Type II collagen.

The solubilization treatments also remove from the collagen dead cartilage cells, proteoglycans, glycosaminoglycans, such as hyaluronic acid, and other associated proteins and molecules. The treatments effectively purify the collagen and yield greater than 90% pure collagen. The collagen can then be reconstituted to provide sufficient structural stability for use as a scaffold by imparting crosslinking in the collagen and can then be lyophilized to form a fleece-like matrix on which cells can be grown and retained.

Alternatively, the matrix composition may be formed from recombinantly produced Type II collagen. The substantially pure, recombinantly produced Type II collagen is not crosslinked, however, it can have telopeptide regions. It is soluble and can be formed into a fleece-like matrix.

The matrix may have two smooth surface sides or one of its sides may have a rough surface. A smooth surface on the matrix typically impedes tissue ingrowth, while a rough surface promotes cell ingrowth. The surface properties of the matrix may be altered by slowly adding an alcohol, such as ethanol (in a 10–30% solution), in the lyophilization mixture.

Further, the consistency of the matrix can vary from a liquid or gel-like form to a solid, fleece-like, flexible form, depending on contact with a physiologically compatible thickening or gelling agent, exposure to heat, or by a chemical reaction, such as an enzymatic reaction (i.e., treatment with pepsin) or one with a crosslinking agent. The resulting properties of the matrix will vary accordingly. The matrix should have a strength ($F_{max}$ in Newtons) of between about 0.7 and about 1.3, preferably about 1.0 Newtons. In addition, the maximum elasticity ($F_{max}$) is from about 4.6% to about 5.6%, from about 0.176 to about 0.184 N/mm$^2$, preferably about 5.1% and about 0.18 N/mm$^2$. These elasticity parameters reflect the strength of the membrane to be used.

The crosslinking agent can be an aldehyde-based biocompatible crosslinking agent or a polyvalent aldehyde, such as glutaraldehyde. Also, the crosslinking agent can be a bifunctional agent with two moieties reacting with the support matrix and its components. Examples of the moieties are aldehydes; ketones; acetals; half acetals; moieties which are available for oxidative coupling, such as phenolic groups; quinones, such as flavoids; carboxylic groups; and activated carboxylic acids. Also, ethyl-dimethyl-aminopropylcarbodiimide (EDC) may be used as a crosslinking agent.

Preferred crosslinking agents are chemical compounds containing two aldehyde groups. The aldehyde groups promote crosslinking by bridging Lysine residues on the telopeptide portion of the Type II collagen. A specifically preferred crosslinking agent is the bioflavonoid, cyanidanol. The type of crosslinking agent to be used is determined by evaluating its effect on the consistency and physical properties of the matrix and its physiological compatibility with the area of the body in which the matrix and cells are to be implanted.

Crosslinking can also be accomplished by heating or subjecting the composition to radiation. In addition, applying heat or radiation to the composition can increase the degree of crosslinking in a composition which is already chemically crosslinked, for example, by prior addition of an aldehyde-containing compound. The heat-induced increase in crosslinking can also cause the composition to be less gel-like and more rigid.

The matrix of the present invention is especially useful in tight or narrow joints, such as the human hip, where conventional collagen membranes cannot be placed. When treating a tight joint, the matrix can be manipulated to be placed at the site of the joint, and it will then remain at the site after placement. Also, the matrix may incorporate additional types of cells, e.g., osteocytes for treatment of bone damage along with a suitable growth stimulating enzyme.

The gel form of the matrix loaded with cells, such as chondrocyte cells, can be used for incorporation, such as by injection, into tight joints or other areas where insertion of a fleece-like matrix (in which the collagen molecules are already crosslinked) would be difficult or impossible. As the gel-like matrix is injected into a site in the body, a crosslinking agent can be injected simultaneously at that site in order to provide crosslinking in the Type II collagen of the matrix. This crosslinking would cause the matrix to become more rigid for increased structural integrity and stability at the site of implantation. Any suitable biocompatible crosslinking agent should be useful, including the agents described above as being incorporated into the matrix before implantation into the body and those used with, for example, Type I collagen matrices.

Because Type II collagen provides a major scaffolding component of native cartilage, the matrix of the present invention therefore imitates natural cartilage tissue. In one embodiment of the present invention, the support matrix along with cells, such as chondrocyte cells, form an implantable article for placing in animals for repair of an injury, such as cartilage damage. If cell differentiation is guided by a surrounding matrix, redifferentiation of chondrocytes should reach an optimum when grown on a Type II collagen matrix, as in the present invention.

Chondrocyte cells, which may be autologous or homologous, can be retained on the support matrix to be used for the treatment of cartilage defects in joints. Chondrocyte cells can be grown directly on the support matrix or in standard dishes and/or loaded onto the matrix before (typically, two to three days before) use. The chondrocyte cell-loaded support matrix, i.e., the implantable article, is introduced into the joint through an arthroscope, or by minimally invasive or open joint surgery techniques. The implantation method of the invention also contemplates the use of suitable allogenic and xenogenic chondrocyte cells for the repair of a cartilage defect.

The cell-loaded matrix (implant) can be incorporated into various other techniques for effecting or stimulating repair of a bodily defect or damage using various placement and securing devices for implantation. Certain of these techniques and devices are shown in the U.S. patent application of Behrens et al. entitled "METHODS, INSTRUMENTS AND MATERIALS FOR CHONDROCYTE CELL TRANSPLANTATION," Ser. No. 09/373,952, filed Aug. 13, 1999; in U.S. Provisional Application No. 60/096,597, filed Aug. 14, 1998; and U.S. Provisional Application No. 60/146,683, filed Aug. 2, 1999, the entire disclosures of which are incorporated herein by reference.

Thus, the present invention teaches methods and systems for the effective repair or treatment of defects in articular cartilage and bone; osteochondral defects; skin and wound defects; and defects of ligaments, menisci, and vertebral discs. These methods and systems involve the use of an implantable article comprising the reconstituted Type II collagen, cartilage-like matrix of the present invention along with cells, such as chondrocyte cells.

For these purposes, the support matrix of the implant is made of a material, specifically, crosslinked Type II collagen, with sufficient physical integrity to hold a stable form for a period of time to enable the growth of cells thereon both before transplant and after transplant, and to provide a system similar to the natural environment of the cells to optimize cell growth differentiation. Over time, perhaps within two to three months, the matrix is expected to be resorbed in a body of a patient receiving the implant without leaving any significant traces and without forming toxic degradation products. The term "resorbed" is meant to include processes by which the support matrix is broken down by natural biological processes, and the broken down support matrix and degradation products thereof are disposed, for example, through the lymphatics or blood vessels.

GENERAL EXAMPLE

In one embodiment, the process for preparing the support matrix of the present invention includes scraping articular cartilage from the surface of the joint of a large mammal or other animal, such as a horse, pig, cow (or calf), goat, chicken, or kangaroo. The scraped cartilage is frozen and ground in a frozen state, such as in a liquid nitrogen or liquid argon atmosphere. In such an atmosphere, the cartilage is shock frozen to form a powder-like material. Typically, the mass of the ground cartilage is approximately 300 grams wet weight.

The powder-like material is subsequently defatted by one or more washings with a suitable solvent, such as an alcohol, ether, benzene, p-toluene, or other solvent having a high degree of solubility for fat molecules. For example, 300 ml of ethanol (in a 70% solution) may be used. The defatting solution allows for extraction of the fat molecules from the cartilage. The resulting solution containing the fat molecules is allowed to dry, for example, by evaporation at room temperature, or is dried by heating to a temperature of about 50° C. until a solid is obtained.

The defatted cartilage solid is then redissolved in a suitable acidic buffer, such as 0.05M Na-acetate buffer at pH 1.5. The resulting solution is then treated with a proteolytic enzyme, such as aqueous pepsin (0.1 mg/ml), preferably at reduced temperature, such as about 4° C. The enzyme treatment may be repeated up to about 10 times in order to optimize the product yield, but five such repetitions have been found sufficient to achieve a favorable yield.

The treated material is subsequently centrifuged at a temperature between about 4° C. and 10° C., and at a speed of between about 10,000 and 20,000 revolutions per minute (RPM)) for about 30 minutes to about one hour. This may be carried out multiple times to achieve a distinct phase separation. Three such repetitions have achieved a favorable separation.

Once adequate phase separation is obtained, the pellet is discarded and the supernatant obtained from centrifugation (in multiple vials) is pooled. The supernatant is then precipitated using a suitable salt solution and a buffer at a neutral pH, such as potassium chloride (17.5% w/v) in phosphate buffer (0.02M $KH_2PO_4$, pH 7.4), which salts out the precipitate. By "salt out," it is meant to saturate a solution with salt from a salt solution such that a solid is precipitated. In a preferred embodiment of the method of the present invention, about 300 ml of supernatant is obtained from centrifugation, the mass of the precipitate generated from the first centrifugation step is approximately 280 grams, and the potassium chloride is prepared in a total volume of 2 liters of the phosphate buffer.

The precipitate is then centrifuged at a speed of between about 30,000 and about 100,000 RPM for about 30 minutes to about one hour to produce further phase separation to form a pellet, and the resulting supernatant is discarded while the resulting pellet is resuspended in a suitable acidic buffer, such as 0.05% acetic acid (200–500 ml). The concentration of cartilaginous material in the solution is generally greater than 1 mg/ml.

To provide a form of the matrix of the present invention with physical integrity for subsequent handling and manipulation, crosslinking is required, as exemplified below.

A biocompatible crosslinking agent is then added to the cartilage/collagen-containing solution. As discussed above, the specific crosslinking agent can be chosen to achieve a certain consistency and specific physical properties for the matrix, i.e., the strength and elasticity described above. The crosslinking agent is prepared in a suitable neutral buffer, such as 10–40 ml of 0.2M NaCl/0.05M Tris-HCl pH 7.4, to a concentration of 20–100 mg/ml.

The solution containing the crosslinked collagen/cartilage is then lyophilized to obtain a solid. The lyophilization may be repeated after re-soaking with an aqueous solution, such as with 10–20 ml of distilled water (depending on the size of the lyophilized collagen "pellet") at a temperature between about 20° C. and about 60° C., preferably at about 25° C., and at a pressure of about 0.05 mbar. When the temperature is increased within that range, the degree of crosslinking and the corresponding stability of the material increase. In contrast, when the temperature is decreased within that range, the degree of crosslinking and the corresponding stability decrease. A preferred embodiment of the invention incorporates multiple lyophilization steps and yields two smooth surfaces for the ends of the matrix. In addition to the use of a crosslinking agent and exposure to heat, exposure to radiation may be used to increase crosslinking of the collagen.

The lyophilization time varies depending on the volume of the solution to be lyophilized and the size of the pellet that is obtained. For example, a 100 ml solution is lyophilized for about 36 hours to yield a suitably dry pellet-shaped solid. The solid obtained is hydroscopic and contains no more than about 20% water in its polymeric structure. The solid is a bright, white, fleece-like material.

Figure 1:
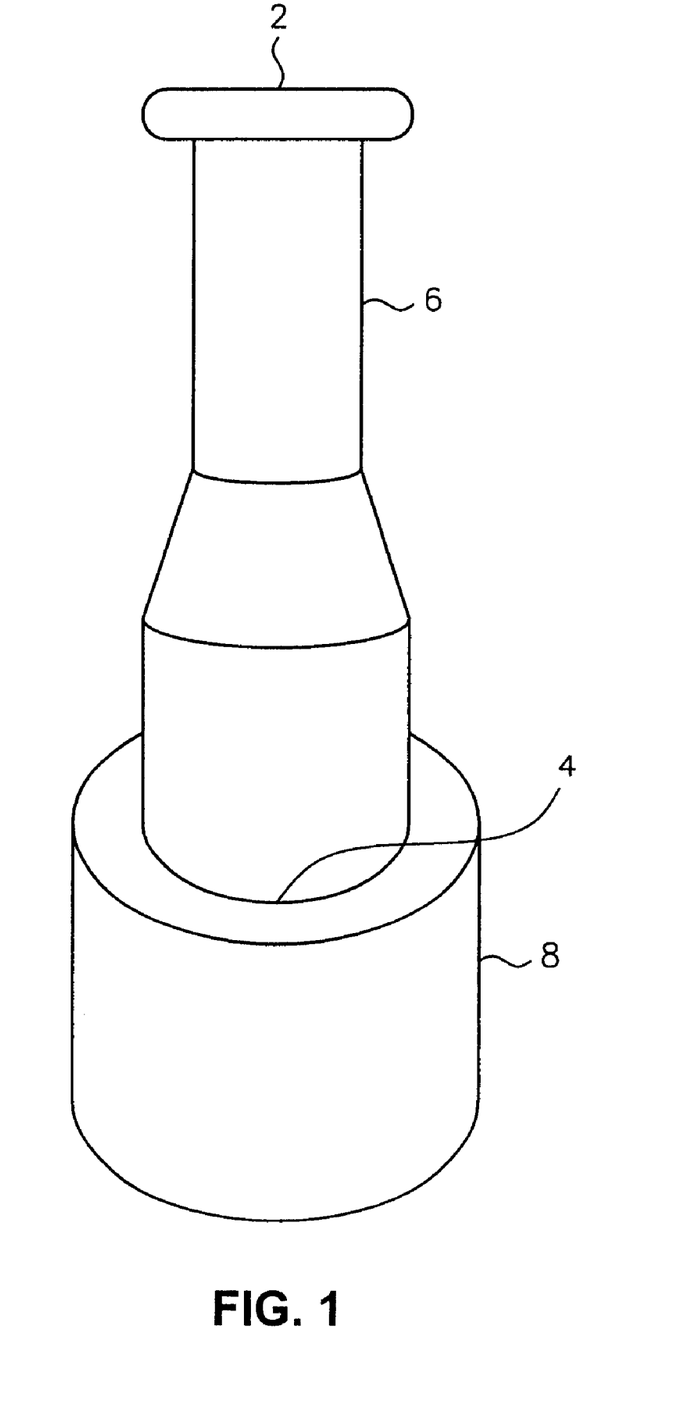
FIG. 1 shows an exemplary pressing device for shaping the matrix into the sheet-like configuration according to the present invention.
Figure 2:
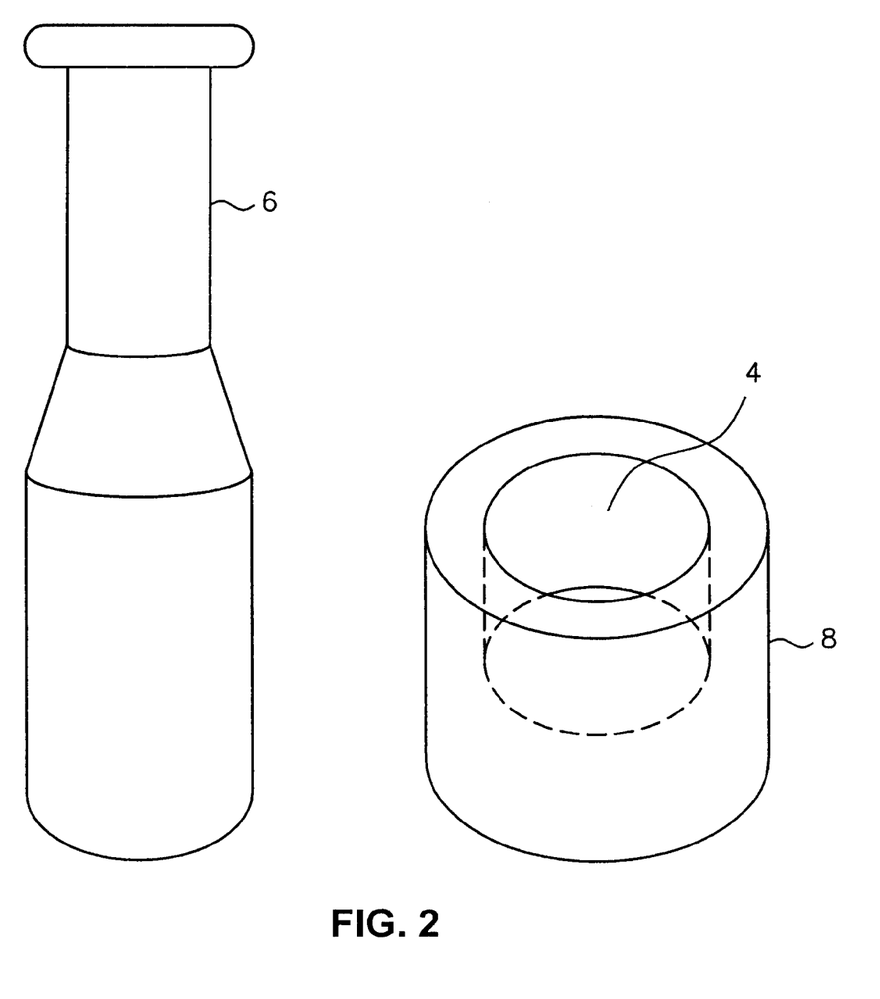
FIG. 2 shows the two components of the exemplary pressing device of FIG. 1 for shaping the matrix into the sheet-like configuration according to the present invention.

This fleece-like material may be pressed mechanically into sheets for use with cells as an implantation article. An example of a pressing machine suitable for this purpose is shown in FIGS. 1 and 2. The machine comprises two non-textured stainless steel mating pieces 6 and 8 with flat mating surfaces. Piece 6 fits within hole 4 of piece 8. The flat bottom surface of piece 6 mates with the flat bottom of hole 4 to provide a pressing action on the fleece-like material placed therebetween. When the fleece-like material is pressed for about 24 hours between these surfaces, the fleece-like sheet becomes more handleable and easier to manipulate. In addition, the sheet is tear resistant.

Alternatively, the pressing device may be any suitable device with mating flat surfaces with enough weight to-continually apply force to the matrix material. The pressing device preferably is made of stainless steel, however, metals and other materials, for example, plastic, glass, or ceramic, with similar mechanical properties to stainless steel may also be used. Generally, a weight of from about 650 to about 850 grams, preferably about 735 grams, for piece 6 is sufficient to press a fleece-like starting piece from about 5 to about 10 mm in thickness and with a surface area of about 19 mm. After pressing, the thickness of the fleece-like sheet is from about 0.5 to about 2.0 mm.

The matrix material of the present invention is sterilized prior to use, such as by radiation (UV or gamma radiation) or by other sterilization procedures, such as by epoxide or ozone sterilization. Radiation sterilization is a preferred method in order to minimize contact of the matrix material by extraneous chemical entities. This final procedure (radiation sterilization) also further stabilizes the collagenous support matrix material.

The support matrix of the present invention, when soaked with cell culture medium, permits the subsequent culturing and growth of chondrocyte cells on the matrix. As indicated above, this growth is possible because the matrix largely comprises Type II collagen which is the principal scaffolding protein for chondrocyte cells in vivo and provides a natural environment for optimal chondrocyte cell growth and differentiation. Chondrocyte cells can be loaded in a sufficient number onto it without significant loss of the biophysical and biomechanical properties of the Type II collagen material. Moreover, the matrix of the present invention can temporarily be deformed, such as for delivery through an arthroscope, without loss of the functional properties of the collagen or loss of its chondrocyte load. This deformation is completely reversible once the matrix is introduced into the joint or is placed on the surface to be treated.

Chondrocyte cells should adhere firmly or integrate into the matrix, and should retain their phenotype or at least have a tendency to redifferentiate after transplantation. Moreover, the resulting cell-matrix-biocomposite should be mechanically stable enough to be handled in operative procedures.

Certain aspects of the present invention are illustrated by the examples which follow. Example 1 illustrates a method of making the novel matrix of the present invention and the growth and retention of chondrocyte cells on the matrix. Example 2 illustrates an additional method of making the novel matrix of the present invention. Examples 3–5 demonstrate the growth and retention of chondrocyte cells on the matrix. Example 6 shows the results of implantation of the matrix containing chondrocyte cells into sheep. The examples are meant by way of illustration and not limitation.

Example 1

For Type II collagen extraction, 300 grams (wet weight) of porcine cartilage is ground under liquid nitrogen to a powder and washed three times with 300 ml of a 70% ethanol solution to defat the collagen. The defatted collagen solution is then dried at room temperature. The resulting collagen solid is redissolved in a 0.05 M sodium acetate solution (pH 1.5) and pepsin is added to a final concentration of 0.1 mg/ml. The solution is then stirred at 4° C. for between 16 and 20 hours and centrifuged at 20,000 RPM for 30 minutes. After one centrifugation cycle, the supernatant obtained (approximately 300 ml) is collected. The remaining pellet is resuspended in a 0.05 M sodium acetate solution and the pepsin treatment, stirring, and centrifugation steps are repeated until most of the pellet is dissolved.

In order to precipitate out a solid containing the Type II collagen, supernatants are pooled (total volume approximately 500 ml) and solid KCl is added to obtain a final concentration of 17.5% KCl. Solid $KH_2PO_4$ is then added to obtain a final concentration of 0.02 M in an aqueous solution. The solution is then centrifuged for 30 minutes at 95,000 RPM and the sediment (pellet) is redissolved in a 0.05% acetic acid solution and dialyzed twice for 16 hours against 5,000 ml of a 0.05% acetic acid solution at 4° C.

An aldehyde-based biocompatible crosslinking agent is added to the dialyzed sample at a concentration of 20–100 mg/ml in 10–40 ml of a 0.2 M NaCl, 0.05 M Tris-HCl solution at pH 7.4. The resulting solution is then lyophilized twice according to the procedure described in the General Example above to obtain a solid. Crosslinking is enhanced by exposure of the resulting solid to UV radiation for 12 hours. The exposure to radiation increases mechanical stabilization of the resulting Type II collagen matrix which is then sterilized by y-radiation.

Chondrocyte cells were enzymatically liberated from knee joint cartilage of adult sheep using collagenase and hyaluronidase (obtained from Sigma, St. Louis, Mo.) and resuspended in culture medium (Ham's F-12) containing 12% fetal calf serum, 50 $\mu$l/ml Penicillin/Streptomycin, 50 $\mu$l/ml Glutamine (all from Biochrom KG, Berlin, Germany), 50 $\mu$l/ml non-essential amino acids (Gibco BRL, Paisley, Scotland), and 2.3 mM $MgCl_2$. Cells were cultured in an 80 $cm^2$ culture flask coated with 0.1% gelatine (Nalge Nunc, Rochester, N.Y.) and incubated at 37° C. in a humidified 5% $CO_2$ environment for 4 to 6 weeks. When the cells reached confluency, they were trypsinized and seeded onto the Type II collagen matrix which was produced as described in this example, at a concentration of approximately $4 \times 10^3$ cells/ml.

Collagen membranes (matrices) were incubated for three days in the above described medium in petri-dishes. Unseeded membranes and chondrocyte cells grown on Thermanox plastic scaffolds (Nunc, Rochester, N.Y.) were used as controls in the experiment.

Membranes were fixed with Bouin's fixative (375 ml of 12% picrinic acid +125 ml of 40% formaldehyde to make up 500 ml of stock solution. For the fixation process, 5 ml of glacial acetic acid is added to 100 ml of stock solution), dehydrated through a graded ethanol series, cut, stained with Masson-Goldner and Mayer's hematoxylin-eosine, and analyzed microscopically. Semi-thin sections (0.5 $\mu$m) of the membrane were stained with azure-II-methylene blue and ultra-thin sections (60 nm) of the membrane were stained with lead citrate.

For transmission electron microscopy (TEM) (in a Philips 400 machine), the specimens were fixed in a 2.5% glutaraldehyde solution in a 0.06M sodium cacodylate buffer (pH 7.35) for 48 to 72 hours at 4° C. The fixed specimens were further processed following routine methods and cut using an Ultracut E microtome (Reichert, Germany).

For scanning electron microscopy, specimens were rinsed with a phosphate buffered saline (PBS) solution (150 mM) at 37° C., fixed as described above for TEM, dehydrated in a graded acetone series, critical point-dried, and sputter-coated with gold-palladium.

Gross morphology of the dry Type II collagen matrices showed a somewhat brittle, paper-like appearance. Shrinking or dissolving of the fleece did not occur during the culturing process. Light microscopy of unseeded Type II collagen matrices revealed a 3-dimensional porous architecture with a differing pore size. Cell detritus or lacunae could not be detected.

Figure 5:
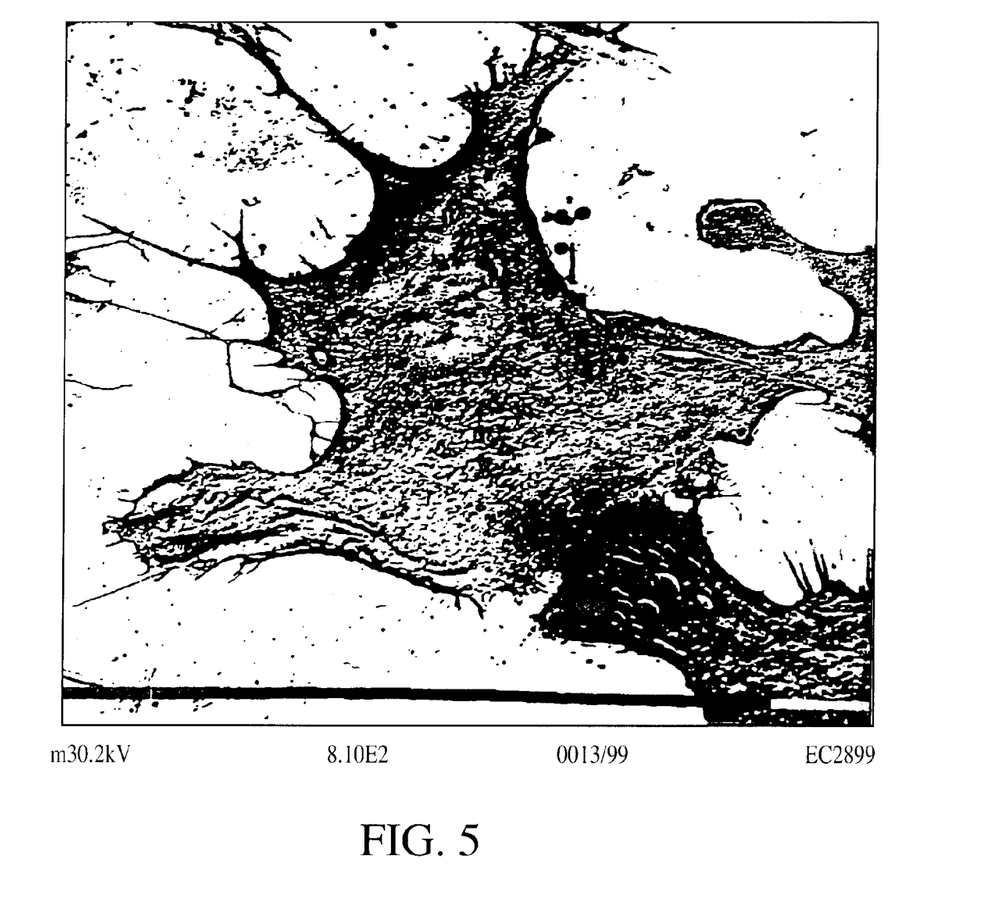
FIG. 5 shows a scanning electron microphotograph of chondrocytes grown on plastic surfaces.

Chondrocytes grown on plastic surfaces exhibited a dense monolayer of spinocellular, fibroblast-like cells with ovoid nuclei and numerous intercellular contacts. In transmission electron microscopy, these cells showed somewhat roundish nuclei, a sparse endoplasmic reticulum, and some mitochondria. As shown in FIG. 5, scanning electron microscopy revealed large flattened cells.

Figure 6:
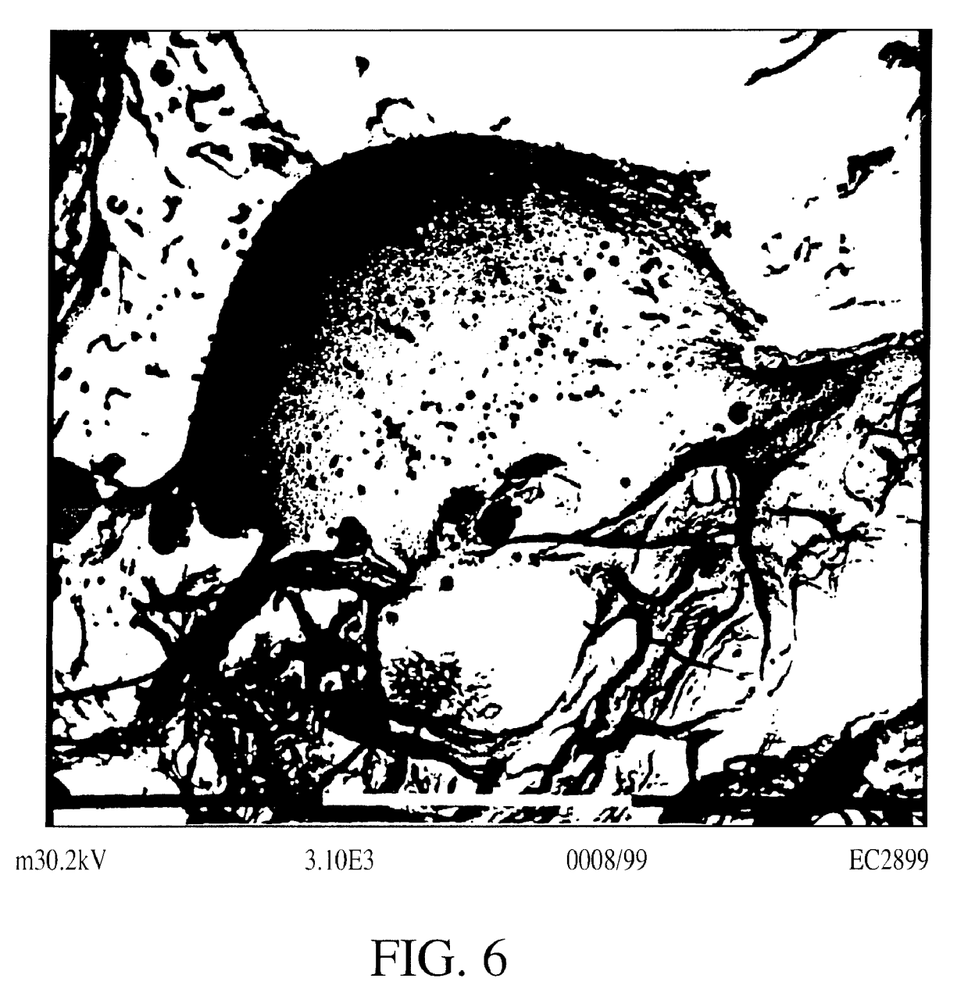
FIG. 6 shows a transmission electron microphotograph of chondrocytes seeded on the matrix of the present invention.

Chondrocytes seeded on Type II collagen matrices formed a membrane of multi-layered cell sheets with numerous cells establishing themselves within the membrane forming processes to entangle with the interconnecting Type II collagen fibers, as shown on TEM in FIG. 6. The ultrastructure of these cells resembled a more chondrocyte-like appearance than a fibroblastic cell type. Most of the cells were spherical with irregular nuclei, granular endoplasmic reticulum, and prominent Golgi fields. Some cells contained high amounts of glycogen and some showed small extruding vesicles on their surfaces.

Comparison of the above mentioned morphological differences between the cells grown on plastic surfaces and on the collagen Type II matrix is strongly suggestive that the chondrocytes grown on the collagen Type II matrix will re-differentiate.

The studies in this example show that in vitro production of autologous cartilage-like tissue can be established using the Type II collagen matrix of the present invention. The resulting implantable article carries active chondrocyte cells with the potential to grow into and repair cartilage defects. The mechanical stability of the article provides for easy handling, so that it can be glued into cartilage defects.

Example 2

300 grams (wet weight) of articular cartilage scraped from calf joints were ground under liquid nitrogen to a powder-like material. The powder was subsequently defatted by 3 washings, each with 300 ml of 70% ethanol, and dried at room temperature. The solid was redissolved in 0.05M Na-acetate buffer, pH 1.5, and subjected to repetitive treatments with pepsin (0.1 mg/ml) in the cold. The treatment was continued for 16–20 hours. After three rounds of centrifugation at between about 4° C. and 10° C. and 10,000–20,000 RPM for about 30 minutes to about one hour, the supernatant was pooled and precipitated by addition of potassium chloride (17.5%) in phosphate buffer. The precipitate was collected by centrifugation at 30,000–40,000 RPM for 45 minutes and resuspended in 0.05% acetic acid to an approximate concentration of greater than 1 mg/ml.

The resulting solution was then dialyzed against 3×5 liters of dilute acetic acid (0.05%) for 16 hours to remove any excess salt. 10–40 ml of the crosslinking agent glutaraldehyde (prepared in 0.2M NaCl/0.05M Tris-HCl pH 7.4, at a concentration of 50 mg/ml) was added to the dialyzed sample. This formed a homogeneous solution which was lyophilized, resoaked with distilled water, and lyophilized again.

The resulting fleece-like material was pressed mechanically into sheets using the device as shown in FIGS. 1 and 2 and sterilized by UV and gamma radiation. Other standard procedures for sterilization which do not damage the matrix could also be used. The sterilization procedure further stabilized the collagenous material.

Example 3

Chondrocytes were grown in minimal essential culture medium containing HAM's F12 and 15 mM Hepes buffer and 5 to 7.5% autologous serum in a $CO_2$ incubator at 37° C. and handled in a Class 100 laboratory at Verigen Transplantation Service ApS, Copenhagen, DK or at the University of Lübeck, Lübeck, Germany. Other compositions of culture medium, such as calf serum, could also have been used for culturing the chondrocyte cells. The cells were trypsinized using trypsin EDTA (trypsin: 2.5% solution without $Ca^{2+}$ and $Mg^{2+}$ in phosphate buffered saline (PBS); EDTA: 1% solution without $Ca^{2+}$ and $Mg^{2+}$ in PBS; the final solution contains 0.05% trypsin) for 5–10 minutes and counted using Trypan Blue viability staining in a Bürker-Türk chamber. The cell count was adjusted to $7.5 \times 10^5$ cells per ml. One NUNCLON™ plate was uncovered in the Class 100 laboratory.

The matrix of the present invention was cut to a suitable size fitting into the bottom of the well in the NUNCLON™ cell culture tray. In this particular case, a circle of a size of approximately 4 cm (but this could have been any size permissible for the experiment) was placed under aseptic conditions on the bottom of the well. Approximately $5 \times 10^6$ cells in 5 ml culture medium were placed directly on top of the carrier material and dispersed over the surface. The plate was incubated in a $CO_2$ incubator at 37° C. for 3 days.

At the end of the incubation period, the medium was decanted, and a cold refrigerated 2.5% glutaraldehyde solution, containing 0.1 M sodium salt of dimethylarsinic acid, was added as a fixative. The matrix was then stained with Safranin O for histological evaluation.

It was observed that the chondrocyte cells had arranged in clusters, had started to grow on the carrier, and could not be removed from the carrier by rinsing it with medium or even by mechanically exerting mild pressure on the matrix. It appeared, therefore, that the cells had adhered to the matrix.

Example 4

Chondrocyte cells were grown in minimal essential culture medium containing HAM's F12 and 15 mM Hepes buffer and 5 to 7.5% autologous serum in a $CO_2$ incubator at 37° C. and handled in a Class 100 laboratory at Verigen Transplantation Service ApS, Copenhagen, DK or at the University of Lübeck. Other compositions of culture medium could have been used for culturing the chondrocytes. The cells were trypsinized using trypsin EDTA (having the same concentrations as in Example 3 above) for 5–10 minutes and counted using Trypan Blue viability staining in a Bürker-Türk chamber. The cell count was adjusted to $5 \times 10^5$ cells per ml. One NUNCLON™ plate was uncovered in the Class 100 laboratory.

The novel matrix of the present invention was cut to a suitable size fitting into the bottom of the well in the NUNCLON™ cell culture tray. In this particular case, a circle of a size of approximately 4 cm (but this could have been any size permissible for the experiment) was placed under aseptic conditions on the bottom of the well. Approximately $5 \times 10^5$ cells in 5 ml culture medium were placed directly on top of the carrier material and dispersed over the surface. The plate was incubated in a $CO_2$ incubator at 37° C. for 3 weeks.

At the end of the incubation period, the medium was decanted, and a cold refrigerated 2.5% glutaraldehyde solution containing 0.1 M sodium salt of dimethylarsinic acid was added as a fixative. The matrix was then stained with Safranin O for histological evaluation. For immunohistochemistry analysis, collagen membranes were fixed in methanol-acetone and stained for aggrecane and Type II collagen using rabbit anti-human type II collagen and mouse anti-humane aggrecane. Primary antibodies were visualized using fluorescent secondary antibodies.

During the three weeks, chondrocytes had grown and multiplied on the matrix, building clusters in the centers of the carrier which had lined up along the surface.

Example 5

Chondrocyte cells were grown in minimal essential culture medium containing HAM's F12 and 15 mM Hepes buffer and 5 to 7.5% autologous serum in a $CO_2$ incubator at 37° C. and handled in a Class 100 laboratory at Verigen Transplantation Service ApS, Copenhagen, DK or at the University of Lübeck. Other compositions of culture medium could have been used for culturing the chondrocyte cells. The cells were trypsinized using trypsin EDTA (same concentration as in Example 3 above) for 5–10 minutes and counted using Trypan Blue viability staining in a Bürker-Türk chamber. The cell count was adjusted to $5 \times 10^5$ cells per ml. One NUNCLON™ plate was uncovered in the Class 100 laboratory.

The matrix of the present invention was cut to a suitable size fitting into the bottom of the well in the NUNCLON™ cell culture tray. In this particular case, a circle of a size of approximately 4 cm (but this could have been any size permissible for the experiment) was placed under aseptic conditions on the bottom of the well. Approximately $5 \times 10^5$ cells in 5 ml culture medium were placed directly on top of the carrier material and dispersed over the surface. The plate was incubated in a $CO_2$ incubator at 37° C. for 3 weeks.

The whole matrix was incubated with collagenase for 16 hours. The material was taken up in medium and centrifuged. Cells were seeded on a NUNCLON™ plate and an aliquot counted using Trypan Blue viability staining in a Bürker-Türk chamber. The total calculated cell number was found to be $6 \times 10^6$ and the viability was greater than 95%.

Example 6

Animal studies were performed in the facilities of the University of Lübeck. Two sheep had previously received 4 defined 7 mm diameter round lesions of the cartilage of the knee joint. All interventions were performed in i.v. Ketanest/Rompun total anaesthesia. Two holes had been placed in the cartilage of the weight-bearing areas of the medial femur condyle and 2 additional holes were drilled in the area of the femuropatellar and tibiofemural articulations. In each of these two areas, one of the two holes was drilled through the tidemark while in the other, the tidemark was left intact.

At the same time, a piece of cartilage had been harvested from a non-weight bearing area. The chondrocytes from this cartilage were grown on a matrix according to Example 3 for a period of six weeks. The chondrocyte loaded matrix was then re-implanted. The sheep were kept isolated and the knee was kept in a fixed dressing for one week. Afterwards, the sheep was free to move around. Evaluation of the joint showed a healing of the defect, the attachment of the graft, and the regeneration of the cartilage.

While this invention has been described with respect to specific embodiments thereof, it is not limited thereto. In its most general sense, this invention encompasses a Type II collagen support matrix, reconstituted from tissue or any other suitable material after being solubilized, and preferably flexible and resorbable in an animal body. The support matrix acts as a support for living cells grown thereon and attached thereto. Such attachment may be by virtue of cell growth penetrating the surface of the matrix. Preferably, also the support matrix provides sufficient physical integrity to the implantable article to facilitate its manipulation, such as the manipulation necessary to implant it into a living body.

It will be appreciated by persons skilled in the art that numerous variations and/or modifications may be made to the invention shown in the specific embodiments without departing from the spirit and scope of the invention, as broadly described.

What is claimed:

1. A Type II collagen-based matrix comprising reconstituted Type II collagen formed from solubilized articular cartilage tissue, wherein the matrix is fleece-like, implantable in an animal body, and adapted, when disposed in the animal body, to be resorbed into the animal body by natural biological processes.

2. The matrix according to claim 1 further comprising a crosslinking agent having an aldehyde moiety and wherein the cartilage tissue is from an animal selected from the group consisting of a horse, pig, cow, calf, goat, chicken, and kangaroo.

3. The matrix according to claim 1 further comprising a bifunctional crosslinking agent and wherein the cartilage tissue is from an animal selected from the group consisting of a horse, pig, cow, calf, goat, chicken, and kangaroo.

4. The matrix according to claim 3 wherein the animal is a cow, the crosslinking agent is cyanidanol, and the matrix is a support matrix.

5. The matrix according to claim 4 wherein the matrix is a sheet-like member capable of supporting growth of chondrocyte cells and at least one side of the matrix has a smooth surface.

6. An implantable article for cartilage repair in an animal body comprising the matrix according to claim 5 and chondrocyte cells retained on the matrix, wherein the sheet-like member is capable of providing physical integrity to the implantable article to facilitate manipulation thereof.

7. The implantable article according to claim 6, wherein the implantable article is reversibly deformable.

8. A reconstituted Type II collagen-based matrix from solubilized articular cartilage tissue produced by the steps of:

(a) isolating cartilage tissue from an animal;
(b) solubilizing the tissue;
(c) reconstituting the tissue;
(d) crosslinking the tissue;
(e) lyophilizing the material to form a fleece-like material; and
(f) sterilizing the material to form the matrix.

* * * * *